United States Patent
Bristow

(10) Patent No.: US 12,162,869 B2
(45) Date of Patent: Dec. 10, 2024

(54) TYPE II CRYSTALLINE TOPRAMEZONE SODIUM SALT HYDRATE, PREPARATION METHOD THEREFOR AND USE THEREOF

(71) Applicant: Rotam Agrochem International Company Limited, Chai Wan (HK)

(72) Inventor: James Timothy Bristow, Chai Wan (HK)

(73) Assignee: ALBAUGH, LLC, Ankeny, IA (US)

( * ) Notice: Subject to any disclaimer, the term of this patent is extended or adjusted under 35 U.S.C. 154(b) by 156 days.

(21) Appl. No.: 17/734,218

(22) Filed: May 2, 2022

(65) Prior Publication Data
US 2023/0348446 A1    Nov. 2, 2023

(51) Int. Cl.
C07D 413/10    (2006.01)
A01N 43/80    (2006.01)
A01P 13/00    (2006.01)

(52) U.S. Cl.
CPC .......... *C07D 413/10* (2013.01); *A01N 43/80* (2013.01); *A01P 13/00* (2021.08); *C07B 2200/13* (2013.01)

(58) Field of Classification Search
None
See application file for complete search history.

(56) References Cited

U.S. PATENT DOCUMENTS

| | | | |
|---|---|---|---|
| 8,017,556 B2 * | 9/2011 | Gebhardt | C07D 413/10 |
| | | | 548/240 |
| 9,045,465 B1 | 6/2015 | von Deyn et al. | |
| 2010/0075853 A1 * | 3/2010 | Krapp | A01N 43/80 |
| | | | 504/271 |

\* cited by examiner

*Primary Examiner* — Bethany P Barham
*Assistant Examiner* — Paul Hoerner
(74) *Attorney, Agent, or Firm* — Dickinson Wright PLLC

(57) ABSTRACT

A type II crystalline topramezone sodium salt hydrate, a preparation method of the type II crystalline topramezone sodium salt hydrate and the use thereof in herbicidal compositions is provided. An X-ray powder diffraction pattern of the hydrate recorded by Cu-Kα radiation at 25° C. shows at least 3 of the following reflections at 2θ values:

| | |
|---|---|
| 2θ=9.63±0.2° | (1) |
| 2θ=11.00±0.2° | (2) |
| 2θ=11.97±0.2° | (3) |
| 2θ=13.13±0.2° | (4) |
| 2θ=14.36±0.2° | (5) |
| 2θ=15.37±0.2° | (6) |
| 2θ=17.24±0.2° | (7) |
| 2θ=18.01±0.2° | (8) |
| 2θ=19.12±0.2° | (9) |
| 2θ=19.65±0.2° | (10) |
| 2θ=22.03±0.2° | (11) |
| 2θ=23.20±0.2° | (12) |
| 2θ=25.29±0.2° | (13) |
| 2θ=27.29±0.2° | (14) |
| 2θ=27.93±0.2° | (15) |
| 2θ=28.90±0.2° | (16). |

18 Claims, 3 Drawing Sheets

TYPE II CRYSTALLINE TOPRAMEZONE SODIUM SALT HYDRATE, PREPARATION METHOD THEREFOR AND USE THEREOF

TECHNICAL FIELD

The present invention relates to the field of organic synthesis, in particular to a type II topramezone sodium salt hydrate, a preparation method therefor and the use thereof as a herbicidal composition.

BACKGROUND ART

Topramezone is a new type of highly selective pyrazolone benzoate herbicide developed by BASF, Germany. It belongs to a p-hydroxyphenylpyruvate dioxidase (HPPD) inhibitor, which can effectively control the gramineae weeds and broadleaf weeds in the corn fields all over the world.

U.S. Pat. No. 9,045,465 B discloses the structures of topramezone and inorganic salts thereof and the preparation method of topramezone potassium salt analogs. In a preparation embodiment disclosed in the '465 patent, the preparation of the topramezone potassium salt analog comprises using anhydrous dioxane as a solvent and triethylamine as an acid binding agent, and butting the methylsulfonyl chloride with 5-hydroxypyrazole, and then adding potassium carbonate into the system for reflux to obtain a potassium salt of a topramezone analog. If the next step of acid regulation is not carried out, the anhydrous substance form of topramezone salt will be obtained after removing the solvent.

However, experiments have found when the anhydrous substance of topramezone sodium salt is processed into a solid preparation, which is easy to agglomerate during jet pulverization, and the dust is large; moreover, the preparation is difficult to process, for example, it is easy to cream when preparing SG, which makes the granulation difficult. Therefore, the anhydrous substance of topramezone sodium salt has limitations in the application of preparations.

In US 2010075853 A, an aqueous preparation of topramezone sodium salt and its pharmacodynamic study are reported. Upon comparison, the activity of topramezone sodium salt is equivalent to or even higher than that of topramezone acid. However, the water preparation has some shortcomings, for example, its content is limited by the solubility of the active ingredient in water and can't be high.

In the study, the applicant also found the 2.5 water crystalline form of topramezone sodium salt, and defined the 2.5 water topramezone sodium salt hydrate as crystal form I. After single crystal diffraction analysis, the crystalline hydrate is an orthorhombic crystal with the following parameters:

| Parameters | Hydrate |
|---|---|
| Space group | Pbcn |
| a | 2563.60(15) pm |
| b | 953.24(7) pm |
| c | 1566.96(10) pm |
| α | 90° |
| β | 90° |
| γ | 90° |
| Volume | 3829.2(4) am$^3$ |
| Z | 4 |

The parameters shown in the table have the following meanings:
a, b, c=edge length of unit cell
α, β, γ=corresponding angles
Z=number of molecules in the unit cell In the preparation of solid preparations containing topramezone, the crystalline form I of the topramezone sodium salt can be better granulated compared with the anhydrous substance of the topramezone sodium salt. With the heat storage experiment of the preparation product, it is found that the preparation prepared by using type I topramezone sodium salt hydrate is more stable than the preparation based on the anhydrous substance thereof. However, the preparation of type I topramezone sodium salt hydrate requires standing in water or a water-containing mixed solvent at −10° C.-15° C. for 10-48 h to complete the crystallization.

Therefore, the preparation of type I topramezone sodium salt hydrate usually requires long-time crystallization at low temperature, the cost is high, and the industrial application is limited.

SUMMARY OF THE INVENTION

One aspect of the invention provides a type II crystalline topramezone sodium salt hydrate comprising 0.5-2.0 moles of water. An X-ray powder diffraction pattern of the hydrate recorded by using Cu-Ka radiation at 25° C. shows at least 3 of the following reflections at 2θ values in any combination:

$2\theta = 9.63 \pm 0.2°$ (1)

$2\theta = 11.00 \pm 0.2°$ (2)

$2\theta = 11.97 \pm 0.2°$ (3)

$2\theta = 13.13 \pm 0.2°$ (4)

$2\theta = 14.36 \pm 0.2°$ (5)

$2\theta = 15.37 \pm 0.2°$ (6)

$2\theta = 17.24 \pm 0.2°$ (7)

$2\theta = 18.01 \pm 0.2°$ (8)

$2\theta = 19.12 \pm 0.2°$ (9)

$2\theta = 19.65 \pm 0.2°$ (10)

$2\theta = 22.03 \pm 0.2°$ (11)

$2\theta = 23.20 \pm 0.2°$ (12)

$2\theta = 25.29 \pm 0.2°$ (13)

$2\theta = 27.29 \pm 0.2°$ (14)

$2\theta = 27.93 \pm 0.2°$ (15)

$2\theta = 28.90 \pm 0.2°$ (16).

Another aspect of the invention provides a method for preparing the type II crystalline topramezone sodium salt hydrate comprising 0.5-2.0 moles of water. The method comprises the following steps: 1) stirring an aqueous solution of topramezone sodium salt while heating the solution to dissolve the topramezone sodium salt completely, and filtering off insoluble matters; 2) concentrating the filtrate obtained in step 1) under reduced pressure and while heating to remove water, and oven-drying an obtained crude product to obtain the topramezone sodium salt monohydrate.

Another aspect of the invention provides a method for preparing the type II crystalline topramezone sodium salt hydrate comprising 0.5-2.0 moles of water. The method comprises the following steps: 1) suspending a mixture of an anhydrous substance of topramezone sodium salt and the type II crystalline topramezone sodium salt in water of a co-solvent; and 2) separating the type II topramezone sodium salt hydrate.

Yet another aspect of the invention provides a method of controlling the growth of undesired plants by applying the type II crystalline topramezone sodium salt hydrate to the undesired plants or growing sites thereof.

Another aspect of the invention provides a herbicidal composition, wherein the composition comprises the type II topramezone sodium salt hydrate and at least one of a filler and a surfactant.

Yet another aspect of the invention provides a method of controlling the growth of undesired plants by applying the herbicidal composition to the undesired plants or growing sites thereof.

Another aspect of the invention provides a method for controlling the growth of undesired plants, comprising: (i) before the germination of the undesired plants; (ii) after the germination of the undesired plants; or (iii) both (i) and (ii), applying a herbicidally effective amount of the herbicidal composition to the undesired plants or growing sites thereof.

DETAILED DESCRIPTION OF EXAMPLE EMBODIMENTS

In one aspect of the present invention, a type II crystalline topramezone sodium salt hydrate comprising 0.5-2.0 moles of water, which is defined as topramezone sodium salt crystal form II herein, is provided. The X-ray powder diffraction pattern recorded by using Cu-Ka radiation at 25° C. shows at least 3 of the following reflections at 2θ values in any combination:

$2\theta = 9.63 \pm 0.2°$ (1)

$2\theta = 11.00 \pm 0.2°$ (2)

$2\theta = 11.97 \pm 0.2°$ (3)

$2\theta = 13.13 \pm 0.2°$ (4)

$2\theta = 14.36 \pm 0.2°$ (5)

$2\theta = 15.37 \pm 0.2°$ (6)

$2\theta = 17.24 \pm 0.2°$ (7)

$2\theta = 18.01 \pm 0.2°$ (8)

$2\theta = 19.12 \pm 0.2°$ (9)

$2\theta = 19.65 \pm 0.2°$ (10)

$2\theta = 22.03 \pm 0.2°$ (11)

$2\theta = 23.20 \pm 0.2°$ (12)

$2\theta = 25.29 \pm 0.2°$ (13)

$2\theta = 27.29 \pm 0.2°$ (14)

$2\theta = 27.93 \pm 0.2°$ (15)

$2\theta = 28.90 \pm 0.2°$ (16).

Preferably, the X-ray powder diffraction pattern of the type II crystalline topramezone sodium salt hydrate recorded by using Cu-Ka radiation at 25° C. shows at least 4 of the following reflections at 2θ values in any combination, preferably at least 5, more preferably at least 6, further preferably at least 7, and more further preferably at least 8;

$2\theta = 9.63 \pm 0.2°$ (1)

$2\theta = 11.00 \pm 0.2°$ (2)

$2\theta = 11.97 \pm 0.2°$ (3)

$2\theta = 13.13 \pm 0.2°$ (4)

$2\theta = 14.36 \pm 0.2°$ (5)

$2\theta = 15.37 \pm 0.2°$ (6)

$2\theta = 17.24 \pm 0.2°$ (7)

$2\theta = 18.01 \pm 0.2°$ (8)

$2\theta = 19.12 \pm 0.2°$ (9)

$2\theta = 19.65 \pm 0.2°$ (10)

$2\theta = 22.03 \pm 0.2°$ (11)

$2\theta = 23.20 \pm 0.2°$ (12)

$2\theta = 25.29 \pm 0.2°$ (13)

$2\theta = 27.29 \pm 0.2°$ (14)

$2\theta = 27.93 \pm 0.2°$ (15)

$2\theta = 28.90 \pm 0.2°$ (16).

Figure 1:
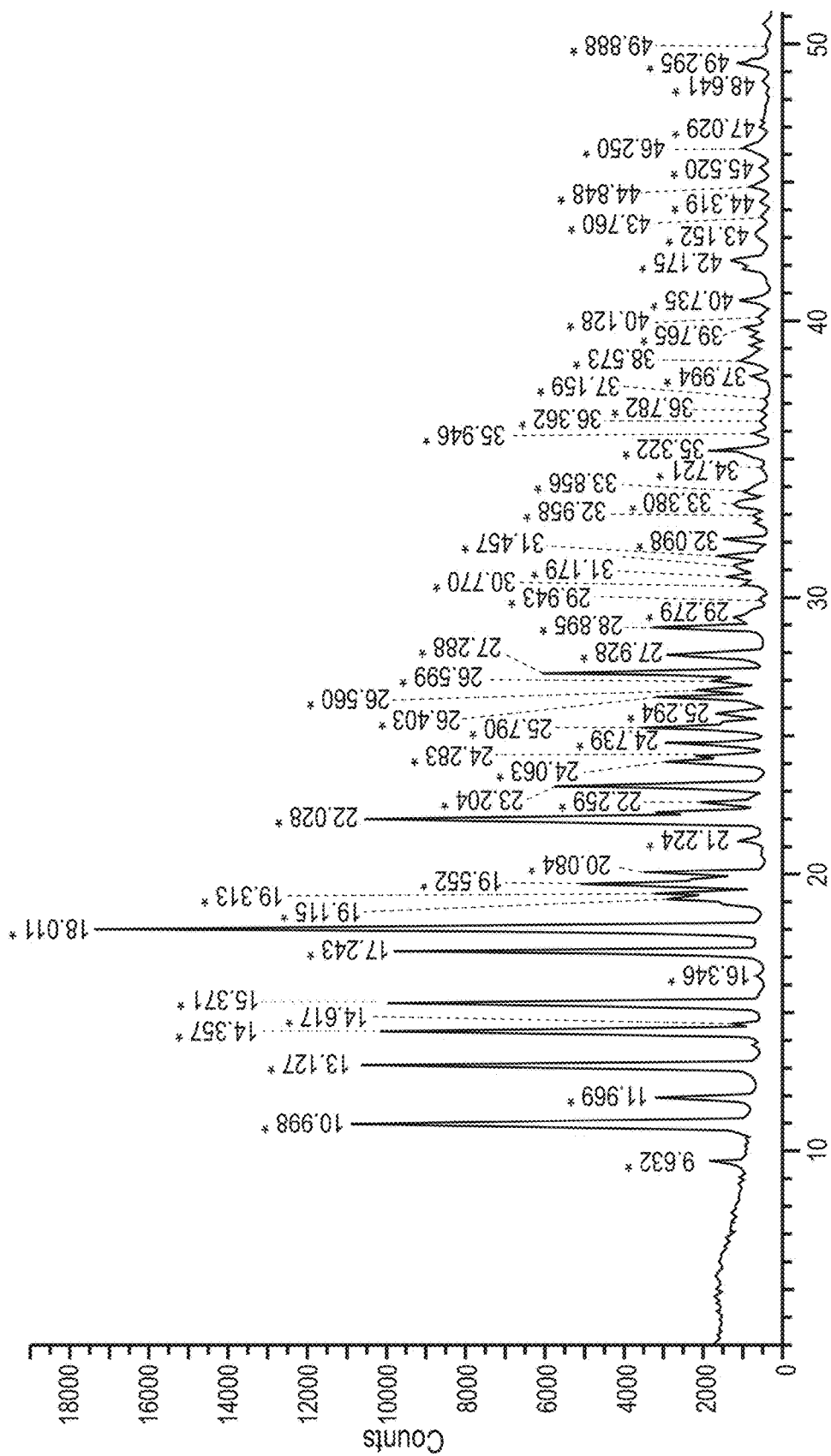
FIG. 1 is an X-ray powder diffraction pattern of the type II crystalline topramezone sodium salt hydrate.

Preferably, the type II crystalline topramezone sodium salt hydrate has an X-ray powder diffraction pattern as shown in FIG. 1.

The type II crystalline topramezone sodium salt hydrate can be further characterized by means of infrared spectroscopy.

Preferably, the type II crystalline topramezone sodium salt hydrate exhibits the IR spectrum with characteristic functional group vibration peaks at one or more wave numbers ($cm^{-1}$, ±0.2%) of about 3356.55, 1620.57, 1503.74, 1432.75, 1404.78, 1379.98, 1301.40, 1188.37, 1154.18, 1123.55, 1053.85, 969.44, 919.52, 861.85, 837.01, 787.60, 770.03, 747.13, 652.57, 599.83, and 562.01.

Preferably, the type II crystalline topramezone sodium salt hydrate exhibits the IR spectrum with characteristic functional group vibration peaks at three or more wave numbers (cm-1, ±0.2%) of about 3356.55, 1620.57, 1503.74, 1432.75, 1301.40, 1188.37, 1154.18, 1123.55, 969.44, 919.52, 861.85, 837.01, and 770.03.

Figure 2:
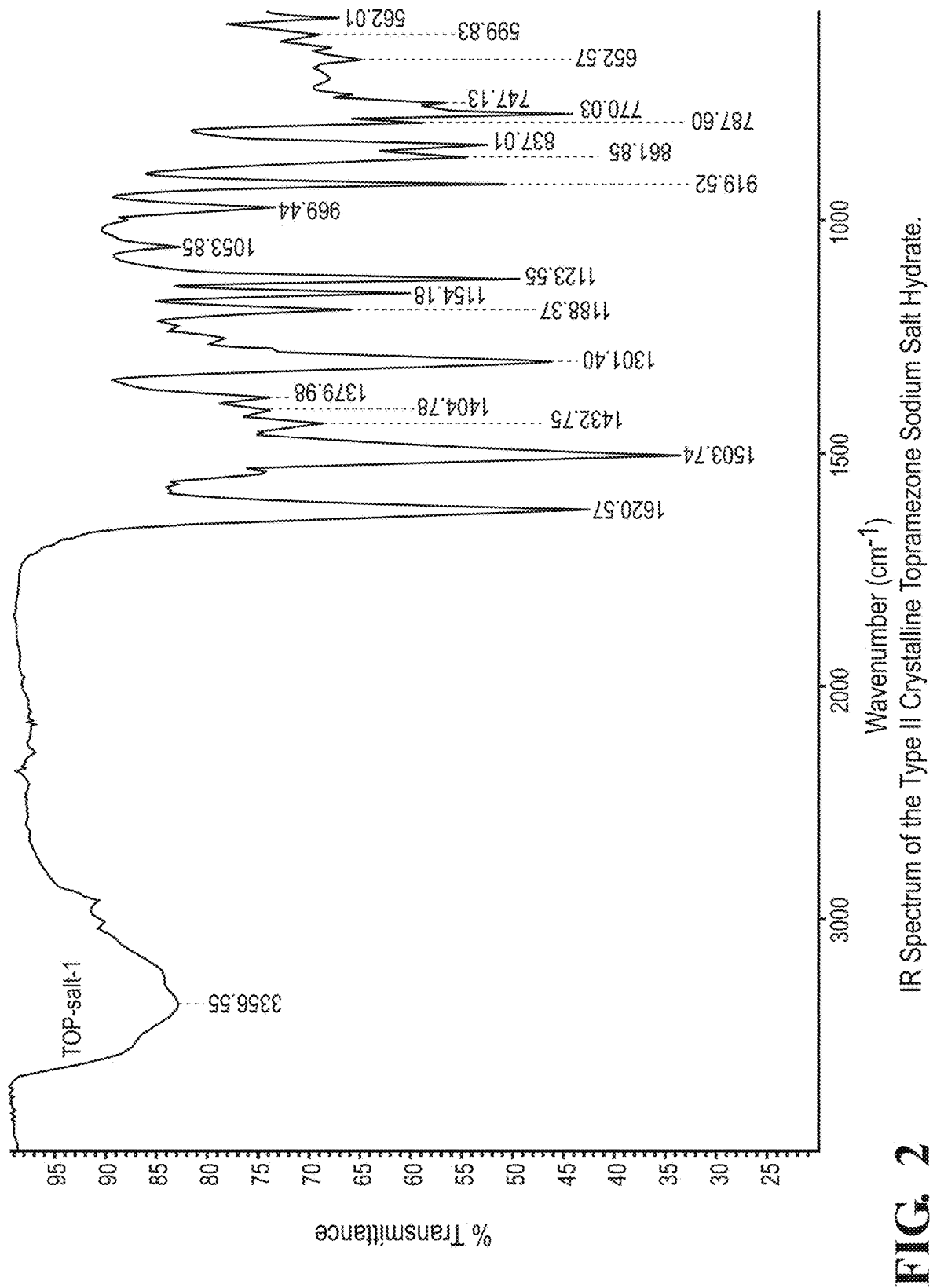
FIG. 2 is an IR spectrum of the type II crystalline topramezone sodium salt hydrate.
Figure 3:
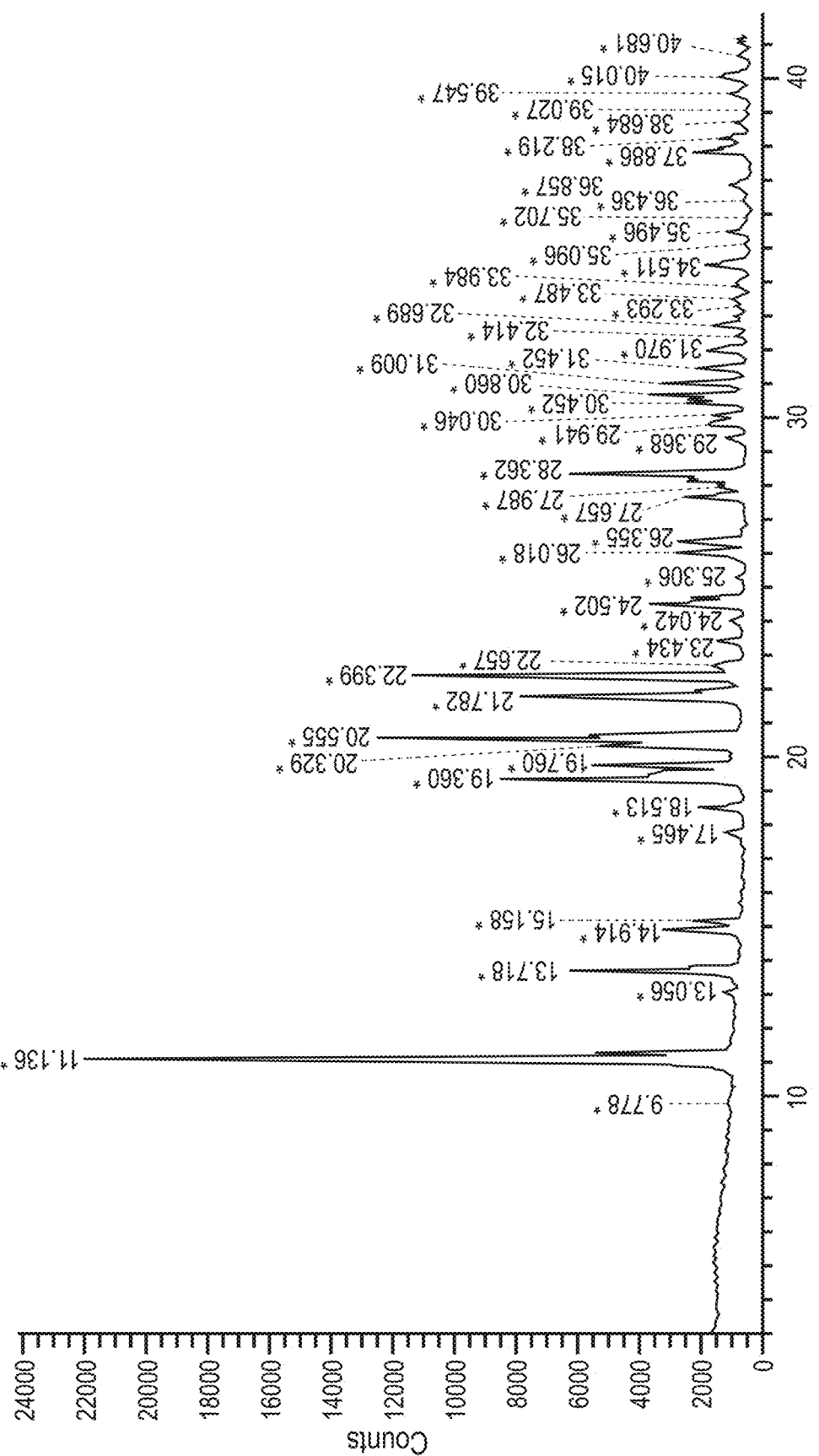
FIG. 3 is an X-ray powder diffraction pattern of the type I crystalline topramezone sodium salt hydrate.

Preferably, the type II crystalline topramezone sodium salt hydrate has an IR absorption spectrum as shown in FIG. 2.

In the preferred embodiment of the first aspect of the present invention, the type II crystalline topramezone sodium salt hydrate is a monohydrate.

The second aspect of the present application provides a method for preparing the type II crystalline topramezone sodium salt hydrate of the present invention. The preparation of the type II crystalline topramezone sodium salt crystalline hydrate can be carried out by the following different methods.

Firstly, when the raw material for preparing the type II crystalline topramezone sodium salt hydrate is the corresponding aqueous solution of topramezone sodium salt, a preferred preparation method comprises stirring a topramezone sodium salt solution under heating to dissolve it completely, filtering out the insoluble matters, and then concentrating same under reduced pressure to remove water, oven-drying the crude product to obtain a topramezone sodium salt monohydrate. The specific process is as follows:

1) stirring the aqueous solution of topramezone sodium salt under heating to dissolve it completely, and filtering off the insoluble matters;
2) concentrating the queous solution of sodium salt obtained in step 1) under reduced pressure and heating to remove water, and oven-drying the obtained crude product to obtain the topramezone sodium salt monohydrate.

In the above step 1), the heating temperature of the aqueous solution of topramezone sodium salt is 20-90° C., preferably 40-80° C.;

in the above step 2), the heating temperature is 20-70° C., preferably 30-60° C.; the oven-drying temperature is 30-60° C., preferably 35-50° C.

The preparation of the aqueous solution of topramezone sodium salt can be achieved by many methods. One method comprises, after the synthesis of the technical topramezone according to the prior art, adding sodium-containing strong bases such as sodium hydroxide or sodium carbonate into the reaction mother liquor for conversion, so as to obtain the aqueous solution of topramezone sodium salt; another method comprises using topramezone and sodium-containing strong bases such as sodium hydroxide or sodium carbonate for salt forming treatment, so as to obtain the aqueous solution of topramezone sodium salt.

When the raw material for preparing the type II crystalline topramezone sodium salt hydrate is the anhydrous substance of topramezone sodium salt, a preferred preparation method comprises suspending the mixture of the anhydrous substance of topramezone sodium salt and the type II crystalline topramezone sodium salt hydrate in the water of a co-solvent; after the crystallization is complete, separating the type II topramezone sodium salt hydrate. The specific process is as follows:

1) suspending a mixture of an anhydrous substance of topramezone sodium salt and the type II crystalline topramezone sodium salt in the water of a co-solvent; and
2) separating the type II topramezone sodium salt hydrate.

In the above step 1), the co-solvent is selected from methanol, ethanol, isopropanol and acetone, and the co-solvent is preferably methanol.

When the raw material for preparing the type II crystalline topramezone sodium salt hydrate is the anhydrous substance of topramezone sodium salt, it can also be dissolved by adding water or a water-containing mixed solvent to the anhydrous substance of topramezone sodium salt, after filtering off the insolubles, the mother liquor is cooled to room temperature, and concentrated under reduced pressure at 20-70° C. to remove water, and the obtained crude product is oven-dried to obtain the type II crystalline topramezone sodium salt hydrate of the present invention.

The characterization of the type II crystalline topramezone sodium salt hydrate of the present invention is carried out by a combination of powder XRD diffraction, Karl Fischer test and IR.

The preparation method of topramezone is known and can be prepared with reference to the method reported in the prior art.

Comparing the preparation processes of different crystal forms of topramezone sodium salt, type II crystalline hydrate does not require long-time crystallization at low temperature. The type I topramezone sodium salt hydrate requires standing in water or a water-containing mixed solvent at −10° C.-15° C., preferably −5° C.-5° C. for 10-48 h to complete the crystallization. Therefore, the energy consumption and cost for preparing type II topramezone sodium salt hydrate are significantly lower than that of the type I topramezone sodium salt hydrate.

Therefore, compared with the topramezone sodium salt crystal form I, the type II crystalline hydrate provided by the present invention does not require long-time crystallization at low temperature, and the energy consumption and cost are significantly reduced.

The type II crystalline topramezone sodium salt hydrate provided by the present invention has storage stability. Compared with the anhydrous substance of topramezone sodium salt, it has significant advantages in preparation processing. The preparation product obtained from the type II crystalline hydrate provided by the present invention has the stability equivalent to or even better than that of the crystal form I.

The third aspect of the present invention provides a herbicidal composition comprising a type II crystalline topramezone sodium salt hydrate, as well as a filler and/or a surfactant.

The type II crystalline topramezone sodium salt hydrate provided by the present invention firstly overcomes the problem that the content of topramezone SL product in the prior art is limited by the solubility of active ingredients, so that it is difficult to make a high-content preparation, thereby reducing the packaging, storage and transportation costs. Secondly, compared with the anhydrous substance of topramezone sodium salt, the type II crystalline topramezone sodium salt hydrate provided by the present invention has obvious advantages in preparation processing; after being processed into a preparation, the preparation product shows better stability in heat storage.

In the herbicidal composition of the present invention, the content of the active ingredients of the type II crystalline topramezone sodium salt hydrate accounts for 1 weight percent (wt. %)-90 wt. %, preferably 10 wt. %-90 wt. %, preferably 20 wt. %-90 wt. %, more preferably 30 wt. %-90 wt. %, more preferably 50 wt. %-90 wt. %, and more preferably 50 wt. %-80 wt. %, based on the total weight of the herbicidal composition.

The dosage form of the herbicidal composition of the present invention is soluble granule (SG), water dispersible granule (WG), wettable powder (WP), oil-based suspension (OD) or dispersible tablet.

The "filler" may be solid or liquid.

Suitable liquid carriers are: including but not limited to water, paraffin, alkylbenzene, alkylnaphthalene, glycerol, triacetin, olive oil, castor oil, linseed oil, sesame oil, corn oil, peanut oil, cottonseed oil, soybean oil, rapeseed oil and coconut oil and mixtures thereof.

Suitable solid carriers may be water soluble or water insoluble. Water-soluble solid carriers include, but are not limited to, salts such as alkali metal phosphates (such as sodium dihydrogen phosphate), alkaline earth metal phosphates, sulfates of sodium, potassium, magnesium and zinc, sodium chloride and potassium chloride, sodium acetate, sodium carbonate and sodium benzoate, sugars and sugar derivatives such as sorbitol, lactose, sucrose and mannitol. Examples of water-insoluble solid carriers include, but are not limited to, clay, synthetic silica and diatomite, calcium silicate and magnesium silicate, titanium dioxide, aluminum oxide, calcium oxide and zinc oxide, and mixtures thereof.

The "surfactant" includes wetting agents, dispersants, thickening agents or mixtures of these surfactants.

The wetting agents include, but are not limited to, alkyl sulfosuccinates, laurates, alkyl sulfates, phosphates, acetylenic diols, ethoxylated fluorinated alcohols, ethoxylated silicone, alkylphenol ethoxylates, benzenesulfonates, alkyl-substituted benzenesulfonates, alkyl α-olefin sulfonates, naphthalenesulfonates, alkyl-substituted naphthalenesulfonates, naphthalenesulfonates, and condensates of alkyl-substituted naphthalenesulfonates and formaldehyde, and alcohol ethoxylates and mixtures thereof. Sodium alkylnaphthalenesulfonate salts are particularly useful for the composition of the present invention.

The dispersants include, but are not limited to, sodium, calcium and ammonium salts of lignosulphonic acid (optionally polyethoxylated); sodium and ammonium salts of maleic anhydride copolymers; sodium salts of condensed phenolsulfonic acid; and naphthalenesulfonic acid-formaldehyde condensates. Lignosulfonates such as sodium lignosulfonate are particularly useful for the composition of the present invention. The thickening agents include, but are not limited to, guar gum, pectin, casein, carrageenan, xanthan gum, alginates, methylcellulose, hydroxyethylcellulose, hydroxypropyl cellulose and carboxymethyl cellulose, and mixtures thereof. Synthetic thickening agents include derivatives of the preceding categories, and also include polyvinyl alcohol, polyacrylamide, polyvinylpyrrolidone, various polyethers, copolymers thereof, and polyacrylic acid and salts thereof, and mixtures thereof.

Other preparation ingredients may also be used in the present invention, such as dyes, desiccants, preservatives, antioxidants, and carriers. These ingredients are known to a person skilled in the art.

The fourth aspect of the present invention provides the use of said herbicidal composition in controlling the growth of undesired plants. The composition obtained by the present invention is particularly suitable for controlling the growth of undesired plants in non-crop areas, especially at high application rates. The herbicidal composition of the present invention acts on gramineae weeds and broadleaf weeds in cereal crops, such as wheat, rye, barley, millet, oats or triticale, and corns without causing any significant damage to crop plants. This effect is particularly observed at low application rates.

In particular, the control objects of the herbicidal composition of the present invention are: *Digitaria sanguinalis*, barnyard grass, *Eleusine indica*, wild *Chenopodium album*, *Setaria viridis*, *Chenopodium album, polygonum, abutilon, Portulaca oleracea, xanthium strumarium*, and nightshade, etc.

The fifth aspect of the present invention provides a method for controlling the growth of undesired plants, wherein the herbicidal composition of the present invention is applied to undesired plants or growing sites thereof.

The application can be carried out by a pre-emergence application method, a post-emergence application method or together with crop seeds, and the herbicidally effective amount of the herbicidal composition can be applied to undesired plants or growing sites thereof. If certain crop plants have poor tolerance to active compounds, a directional spray can be carried out by means of spraying equipment so that the active compounds do not come into contact with the leaves of the sensitive crop plants as much as possible, and at the same time, the active compounds reach the leaves of undesired plants grown underneath or the bare soil surface.

In order to broaden the activity spectrum and obtain synergistic effects, the herbicidal compositions can be mixed before application with a number of representative compounds from the group of other herbicidal or growth-regulating active compounds and then applied in combination, for example by means of a tank-mix method.

In order to aid the understanding of the present invention, the following examples are set forth for the present invention. A person skilled in the art should be clear that the examples are provided only for aiding the understanding of the present invention but should not be regarded as particular limitations to the present invention.

SYNTHETIC EXAMPLES

Example 1. Preparation of Anhydrous Substance of Topramezone Sodium Salt

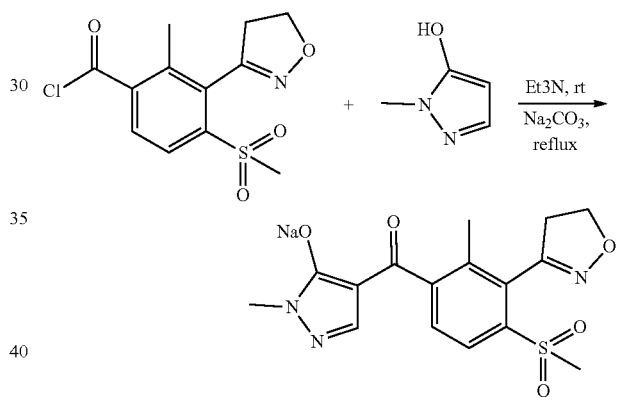

46.2 g (0.15 mol) of 2-methyl-3-(4,5-dihydroisoxazol-3-yl)-4-methylsulfonyl benzoic acid chloride in 450 ml of anhydrous dioxane and 20.7 g (0.2 mol) of triethylamine in 450 ml of anhydrous dioxane are simultaneously added dropwise to 14.7 g (0.15 mol) of 5-hydroxy-1-methylpyrazole and 350 ml of anhydrous dioxane under a protective atmosphere at room temperature. After stirring the reaction mixture at room temperature for 2 hours, it is filtered through silica gel and washed with dioxane. The eluent is concentrated to about 600 ml under vacuum and 32.5 g (0.3 mol) of dry finely powdered sodium carbonate is added. After heating under reflux for 3 hours, the solvent is removed under reduced pressure.

The residue is added to about 800 ml of anhydrous methanol, the insoluble components are filtered out, and the solvent in the mother liquor is removed by means of rotary evaporation to obtain 57.2 g (yield 95%) of the anhydrous substance of topramezone sodium salt (KF: moisture <0.5%).

Example 2: Preparation of Aqueous Solution of Topramezone Sodium Salt 18.5 g (0.06 mol) of 2-methyl-3-(4,5-dihydroisoxazol-3-yl)-4-methylsulfonyl benzoic acid chloride in 180 ml of anhydrous dioxane and 8.3 g (0.08 mol) of triethylamine in 180 ml of anhydrous dioxane are simultaneously added dropwise to 5.9 g (0.06 mol) of 5-hydroxy-1-methylpyrazole and 150 ml of anhydrous dioxane under a protective atmosphere at room temperature. The reaction mixture is stirred at room temperature for 2 hours. At the end of the reaction, 2.9 g (0.07 mol) of 98% flake sodium hydroxide and 200 mL of deionized water are added and stirred for about 1 hour. The reaction solution is layered, the water layer is taken and back-extracted with dioxane for 2-3 times to obtain the aqueous solution of topramezone sodium salt.

Example 3: Preparation of Aqueous Solution of Topramezone Sodium Salt 22.3 g of 98% (0.06 mol) of topramezone and 2.9 g (0.07 mol) of 98% flake sodium hydroxide are weighed, respectively, added to the reactor containing 200 mL deionized water, heated to 60° C. and stirred for about 1 hour, then the insoluble matters are filtered off to obtain the aqueous solution of topramezone sodium salt.

Example 4: Preparation of Type II Crystalline Topramezone Sodium Salt Hydrate 4.0 g of the anhydrous substance of topramezone sodium salt (0.01 mol) obtained in Example 1 is put into a reaction bottle containing 25 ml of water, heated to 50° C. and stirred until the solid is no longer dissolved, and the insoluble matters are removed after filtration. After the filtrate is cooled to room temperature, it is concentrated under reduced pressure to remove water to obtain a yellow solid, which is oven-dried under reduced pressure at 40° C. to obtain 3.8 g of the type II crystalline topramezone sodium salt hydrate. (KF: moisture 4.88%).

The solid particles obtained in this Example are analyzed by X-ray powder diffraction (XRD), and the specific spectrum is shown in FIG. 1. The obtained samples are analyzed by IR and Karl Fischer test, and the specific IR spectrum is shown in FIG. 2.

Example 5: Preparation of Type II Crystalline Topramezone Sodium Salt Hydrate 8.0 g of anhydrous substance of topramezone sodium salt and 1 g of type II crystalline topramezone sodium salt hydrate are added to the reactor containing 40 g of solvent mixture (water: methanol=1:1), heated to 40° C., and stirred for about 10 hours. The mixture obtained is then filtered to obtain a filter cake, and the filter cake is washed with water once. Then the filter cake is dried under reduced pressure at 40° C. to obtain 7.7 g of Form II of Topramezone sodium salt hydrate. (KF: moisture 4.65%)

X-ray powder diffraction (XRD) and IR are used to analyze the obtained topramezone sodium salt solid, and it was found to be the type II crystalline topramezone sodium salt hydrate.

Example 6 Preparation of Type II Crystalline Topramezone Sodium Salt Hydrate

The aqueous solution of topramezone sodium salt obtained in Example 2 is concentrated under reduced pressure at 50° C. to remove water to obtain a yellow solid, which is oven-dried under reduced pressure at 35° C. for 3 hours to obtain about 20.0 g of the type II crystalline topramezone sodium salt hydrate. (KF: moisture 4.78%).

X-ray powder diffraction (XRD) and IR are used to analyze the obtained topramezone sodium salt solid, and it is found as the type II crystalline topramezone sodium salt hydrate.

Example 7 Preparation of Type II Crystalline Topramezone Sodium Salt Hydrate

The aqueous solution of topramezone sodium salt obtained in Example 3 is concentrated under reduced pressure at 50° C. to remove water to obtain a yellow solid, which is oven-dried under reduced pressure at 35° C. for 3 hours to obtain about 21.5 g of the type II crystalline topramezone sodium salt hydrate. (KF: moisture 4.90%).

X-ray powder diffraction (XRD) and IR are used to analyze the obtained topramezone sodium salt solid, and it is found as the type II crystalline topramezone sodium salt hydrate.

PREPARATION EXAMPLES

Application Example 1 Preparation of Water Dispersible Granule (WDG) Preparation All the components listed in table 1 below are uniformly mixed and pulverized into powder with an average particle size of about 3 um by means of a jet mill. A sufficient amount of water is added to obtain an extrudable paste. The resulting paste passes through a die or screen and is extruded to form an extrudate. The wet extrudate is dried at 45° C. or less in a vacuum oven and screened through a 0.7-2 mm screen to obtain product particles.

TABLE 1

| Components | Weight % | | | Function |
| --- | --- | --- | --- | --- |
| | Sample 1 | Sample 2 | Sample 3 | |
| Type II crystalline topramezone sodium salt hydrate (97%) | 33 | 0 | 0 | Active substance |
| Anhydrous substance of topramezone sodium salt (95%) | 0 | 33 | 0 | Active substance |
| Type I crystalline topramezone sodium salt hydrate (97%) | 0 | 0 | 33 | Active substance |
| Calcium polyoxyethylene triphenylphosphate | 6 | 6 | 6 | Dispersant |
| Sodium alkyl naphthalene sulfonate | 2 | 2 | 2 | Dispersant |

TABLE 1-continued

| Components | Sample 1 | Sample 2 | Sample 3 | Function |
|---|---|---|---|---|
| Carboxymethylcellulose | 3 | 3 | 3 | Binder |
| Polyethylene glycol | 3 | 3 | 3 | Disintegrant |
| White carbon black | Making up to 100% | Making up to 100% | Making up to 100% | Auxiliary carrier |

Application Example 2: Preparation of Wettable Powder (WP) Preparation

All the components listed in table 2 below are uniformly mixed and pulverized into powder with an average particle size of about 3 um by means of a jet mill to obtain the wettable powder.

TABLE 2

| Components | Sample 4 | Sample 5 | Sample 6 | Function |
|---|---|---|---|---|
| Type II crystalline topramezone sodium salt hydrate (97%) | 49 | 0 | 0 | Active substance |
| Anhydrous substance of topramezone sodium salt (95%) | 0 | 49 | 0 | Active substance |
| Type I crystalline topramezone sodium salt hydrate (97%) | 0 | 0 | 49 | Active substance |
| Calcium polyoxyethylene triphenylphosphate | 6 | 6 | 6 | Dispersant |
| Alkylphenol polyoxyethylene ether | 3 | 3 | 3 | Dispersant |
| Sodium alkylbenzene sulfonate | 2 | 2 | 2 | Wetting agent |
| White carbon black | 5 | 5 | 5 | Auxiliary carrier |
| Diatomite | Making up to 100% | Making up to 100% | Making up to 100% | Auxiliary carrier |

Application Example 3 Preparation of Soluble Granule (SG) Preparation

All the components listed in table 3 are uniformly mixed, pulverized to below 44 microns by means of ultramicro-pulverization, then an appropriate amount of water is added, mixed by a kneader, and granulated with a rotary shear granulator or other suitable granulators to obtain product particles.

TABLE 3

| Components | Sample 7 | Sample 8 | Sample 9 | Function |
|---|---|---|---|---|
| Type II crystalline topramezone sodium salt hydrate (97%) | 35 | 0 | 0 | Active substance |
| Anhydrous substance of topramezone sodium salt (95%) | 0 | 35 | 0 | Active substance |
| Type I crystalline topramezone sodium salt hydrate (97%) | 0 | 0 | 35 | Active substance |
| Alkyl naphthalene sulfonate | 2 | 2 | 2 | Wetting agent |
| Sodium salt of alkyl naphthalene sulfonate polycondensates | 12 | 12 | 12 | Dispersant |
| Sodium tripolyphosphate | 2 | 2 | 2 | Stabilizer |
| Sucrose | Making up to 100% | Making up to 100% | Making up to 100% | Adjuvant |

Application Example 4 Preparation of Oil-Based Suspension (OD) Preparation

All the components listed in table 4 are added, mixed by high shear and ground by sand mill to obtain a topramezone sodium salt oil-based suspension.

TABLE 4

| Components | Sample 10 | Sample 11 | Sample 12 | Function |
|---|---|---|---|---|
| Type II crystalline topramezone sodium salt hydrate (97%) | 45 | 0 | 0 | Active substance |
| Anhydrous substance of topramezone sodium salt (95%) | 0 | 45 | 0 | Active substance |
| Type I crystalline topramezone sodium salt hydrate (97%) | 0 | 0 | 45 | Active substance |
| Geronol VO/01 | 300 | 300 | 300 | Emulsifier |
| HDK N20 | 30 | 30 | 30 | Thickener |
| BREAK-THRU AF9902 | 15 | 15 | 15 | Defoamer |
| MORWET D-450 POWDER | 40 | 40 | 40 | Wetting dispersant |
| Corn oil | Making up to 100% | Making up to 100% | Making up to 100% | Solvent |

Product Performance Comparison

The preparation samples 1, 2, 3, 4, 5, 6, 7, 8, 9, 10, 11 and 12 prepared in Application examples 1-4 are stored at 54° C. for 2 weeks, respectively. The character changes of each sample before and after storage are compared.

TABLE 5

| Sample No. | Active components and preparations | Character changes |
|---|---|---|
| Sample 1 | Type II crystalline topramezone sodium salt hydrate (WDG) | No change |
| Sample 2 | Anhydrous substance of topramezone sodium salt (WDG) | Partial agglomeration |
| Sample 3 | Type I crystalline topramezone sodium salt hydrate (WDG) | No change |

TABLE 5-continued

| Sample No. | Active components and preparations | Character changes |
|---|---|---|
| Sample 4 | Type II crystalline topramezone sodium salt hydrate (WP) | No change |
| Sample 5 | Anhydrous substance of topramezone sodium salt (WP) | Agglomeration |
| Sample 6 | Type I crystalline topramezone sodium salt hydrate (WP) | No change |
| Sample 7 | Type II crystalline topramezone sodium salt hydrate (SG) | No change |
| Sample 8 | Anhydrous substance of topramezone sodium salt (SG) | Partial creaming |
| Sample 9 | Type I crystalline topramezone sodium salt hydrate (SG) | No change |
| Sample 10 | Type II crystalline topramezone sodium salt hydrate (OD) | No change |
| Sample 11 | Anhydrous substance of topramezone sodium salt (OD) | Agglomeration and sinking to the bottom |
| Sample 12 | Type I crystalline topramezone sodium salt hydrate (OD) | No change |

It can be seen from the table that the characters of the preparation prepared from the type II crystalline topramezone sodium salt hydrate are stable after storage, which is equivalent to that of the preparation prepared from the type I crystalline topramezone sodium salt hydrate. Compared with the agglomeration or creaming phenomenon of the product prepared from the anhydrous substance of topramezone sodium salt, the stability is greatly improved, which is beneficial to industrial production and prolonging the shelf life of products.

What is claimed is:

1. A type II crystalline topramezone sodium salt hydrate comprising 0.5-2.0 moles of water, wherein an X-ray powder diffraction pattern of the hydrate recorded by using Cu-Ka radiation at 25° C. shows at least 3 of the following reflections at 2θ values in any combination:

$2\theta=9.63\pm0.2°$ (1)

$2\theta=11.00\pm0.2°$ (2)

$2\theta=11.97\pm0.2°$ (3)

$2\theta=13.13\pm0.2°$ (4)

$2\theta=14.36\pm0.2°$ (5)

$2\theta=15.37\pm0.2°$ (6)

$2\theta=17.24\pm0.2°$ (7)

$2\theta=18.01\pm0.2°$ (8)

$2\theta=19.12\pm0.2°$ (9)

$2\theta=19.65\pm0.2°$ (10)

$2\theta=22.03\pm0.2°$ (11)

$2\theta=23.20\pm0.2°$ (12)

$2\theta=25.29\pm0.2°$ (13)

$2\theta=27.29\pm0.2°$ (14)

$2\theta=27.93\pm0.2°$ (15)

$2\theta=28.90\pm0.2°$ (16).

2. The type II crystalline topramezone sodium salt hydrate according to claim 1, wherein the X-ray powder diffraction pattern of the hydrate recorded by using Cu-Ka radiation at 25° C. shows at least 4 of the following reflections at 2θ values in any combination:

$2\theta=9.63\pm0.2°$ (1)

$2\theta=11.00\pm0.2°$ (2)

$2\theta=11.97\pm0.2°$ (3)

$2\theta=13.13\pm0.2°$ (4)

$2\theta=14.36\pm0.2°$ (5)

$2\theta=15.37\pm0.2°$ (6)

$2\theta=17.24\pm0.2°$ (7)

$2\theta=18.01\pm0.2°$ (8)

$2\theta=19.65\pm0.2°$ (10)

$2\theta=22.03\pm0.2°$ (11)

$2\theta=27.29\pm0.2°$ (14)

$2\theta=27.93\pm0.2°$ (15)

$2\theta=28.90\pm0.2°$ (16).

3. The type II crystalline topramezone sodium salt hydrate according to claim 1, wherein the hydrate exhibits the IR spectrum with characteristic functional group vibration peaks at one or more wave numbers ($cm^{-1}$, ±0.2%) of about 3356.55, 1620.57, 1503.74, 1432.75, 1404.78, 1379.98, 1301.40, 1188.37, 1154.18, 1123.55, 1053.85, 969.44, 919.52, 861.85, 837.01, 787.60, and 770.03.

4. The type II crystalline topramezone sodium salt hydrate according to claim 3, wherein the hydrate exhibits the IR spectrum with characteristic functional group vibration peaks at three or more wave numbers ($cm^{-1}$, ±0.2%) of about 3356.55, 1620.57, 1503.74, 1432.75, 1301.40, 1188.37, 1154.18, 1123.55, 969.44, 919.52, 861.85, 837.01, and 770.03.

5. The type II crystalline topramezone sodium salt hydrate according to claim 1, wherein the type II crystalline topramezone sodium salt hydrate is a monohydrate.

6. A method for preparing the type II crystalline topramezone sodium salt hydrate comprising 0.5-2.0 moles of water, which comprises the following steps:
   1) stirring an aqueous solution of topramezone sodium salt while heating the solution to dissolve the topramezone sodium salt completely, and filtering off insoluble matters;
   2) concentrating the filtrate obtained in step 1) under reduced pressure and while heating to remove water, and oven-drying an obtained crude product to obtain the topramezone sodium salt monohydrate.

7. The method for preparing type II crystalline topramezone sodium salt hydrate according to claim 6, wherein
   in step 1), the heating temperature of the topramezone sodium salt solution is 20-90° C.;
   in step 2), the heating temperature is 20-70° C.; and the oven-drying temperature is 30-60° C.

8. A method for preparing the type II crystalline topramezone sodium salt hydrate comprising 0.5-2.0 moles of water, which comprises the following steps:
   1) suspending a mixture of an anhydrous substance of topramezone sodium salt and the type II crystalline topramezone sodium salt in water of a co-solvent; and 2) separating the type II topramezone sodium salt hydrate.

9. The method for preparing the type II crystalline topramezone sodium salt hydrate according to claim 8, wherein the co-solvent in step 1) is selected from methanol, ethanol, isopropanol and acetone.

10. The method for preparing the type II topramezone sodium salt hydrate according to claim 8, wherein the co-solvent in step 1) is methanol.

11. A method of controlling the growth of at least one plant selected from the group consisting of gramineae weeds and broadleaf weeds by applying the type II crystalline topramezone sodium salt hydrate according to claim 1 to the at least one plant or growing site thereof.

12. A herbicidal composition, wherein the compositon comprises the type II topramezone sodium salt hydrate according to claim 1, and at least one of a filler and a surfactant.

13. The herbicidal composition according to claim 12, wherein the dosage form of the herbicidal composition is soluble granule (SG), water dispersible granule (WG), wettable powder (WP), oil-based suspension (OD) or dispersible tablet.

14. A method of controlling the growth of at least one plant selected from the group consisting of gramineae weeds and broadleaf weeds by applying the herbicidal composition according to claim 12 to the at least one plant or growing site thereof.

15. The method according to claim 14, wherein the at least one plant includes gramineae weeds and/or broadleaf weeds in corn fields.

16. The method according to claim 14, wherein the at least one plant includes *Digitaria sanguinalis*, barnyard grass, *Eleusine indica*, wild *Chenopodium album*, *Setaria viridis*, *Chenopodium album*, polygonum, abutilon, *Portulaca oleracea*, *xanthium strumarium*, and/or nightshade in corn fields.

17. A method for controlling the growth of at least one plant selected from the group consisting of gramineae weeds and broadleaf weeds, comprising (i) before the germination of the at least one plant; (ii) after the germination of the at least one plant; or (iii) both (i) and (ii), applying a herbicidally effective amount of the herbicidal composition according to claim 12 to the at least one plant or growing site thereof.

18. The type II crystalline topramezone sodium salt hydrate according to claim 1, wherein the X-ray powder diffraction pattern of the hydrate recorded by using Cu-Ka radiation at 25° C. shows at least 5 of the following reflections at 2θ values in any combination:

$2\theta = 9.63 \pm 0.2°$ (1)

$2\theta = 11.00 \pm 0.2°$ (2)

$2\theta = 11.97 \pm 0.2°$ (3)

$2\theta = 13.13 \pm 0.2°$ (4)

$2\theta = 14.36 \pm 0.2°$ (5)

$2\theta = 15.37 \pm 0.2°$ (6)

$2\theta = 17.24 \pm 0.2°$ (7)

$2\theta = 18.01 \pm 0.2°$ (8)

$2\theta = 19.12 \pm 0.2°$ (9)

$2\theta = 19.65 \pm 0.2°$ (10)

$2\theta = 22.03 \pm 0.2°$ (11)

$2\theta = 27.29 \pm 0.2°$ (14)

$2\theta = 27.93 \pm 0.2°$ (15)

$2\theta = 28.90 \pm 0.2°$ (16).

* * * * *